United States Patent [19]
Schulze et al.

[11] Patent Number: 5,599,350
[45] Date of Patent: Feb. 4, 1997

[54] ELECTROSURGICAL CLAMPING DEVICE WITH COAGULATION FEEDBACK

[75] Inventors: Dale R. Schulze, Lebanon; James Giordano, Milford; David Yates, West Chester, all of Ohio

[73] Assignee: Ethicon Endo-Surgery, Inc., Cincinnati, Ohio

[21] Appl. No.: 415,957

[22] Filed: Apr. 3, 1995

[51] Int. Cl.⁶ .................................................. A61B 17/39
[52] U.S. Cl. .............................................. 606/51; 606/171
[58] Field of Search .................... 606/45, 46, 48–52, 606/171

[56] References Cited

U.S. PATENT DOCUMENTS

| | | | |
|---|---|---|---|
| 1,798,902 | 3/1931 | Raney . | |
| 1,881,250 | 10/1932 | Tomlinson . | |
| 2,031,682 | 2/1936 | Wappler et al. | 174/89 |
| 4,375,218 | 3/1983 | DiGeronimo | 128/303.17 |
| 4,655,216 | 4/1987 | Tischer | 128/303.17 |
| 4,671,274 | 6/1987 | Sorochenko | 128/303.14 |
| 4,800,878 | 1/1989 | Cartmell | 606/51 |
| 5,057,107 | 10/1991 | Parins et al. | 606/48 |
| 5,151,102 | 9/1992 | Kamiyama et al. | 606/51 |
| 5,190,541 | 3/1993 | Abele et al. | 606/46 |
| 5,201,900 | 4/1993 | Nardella | 606/157 |
| 5,207,691 | 5/1993 | Nardella | 606/142 |
| 5,360,428 | 11/1994 | Hutchinson, Jr. | 606/45 |
| 5,389,098 | 2/1995 | Tsuruta et al. | 606/41 |
| 5,403,312 | 4/1995 | Yates et al. | 606/50 |
| 5,417,687 | 5/1995 | Nardella et al. | 606/32 |
| 5,445,638 | 8/1995 | Rydell et al. | 606/51 |
| 5,458,598 | 10/1995 | Feinburg et al. | 606/51 |

FOREIGN PATENT DOCUMENTS

| | | |
|---|---|---|
| 0518230A1 | 12/1992 | European Pat. Off. . |
| 0517244A1 | 12/1992 | European Pat. Off. . |
| WO93/08754 | 5/1993 | WIPO . |
| WO94/24949 | 11/1994 | WIPO . |
| WO94/24951 | 11/1994 | WIPO . |

OTHER PUBLICATIONS

Two New Laparoscopic Instruments: Bipolar Sterilizing Forceps and Uterine Manipulator; Corson, Stephen L., Medical Instrumentation, vol. 11, No. 1, (Jan.–Feb. 1977).

*Primary Examiner*—Lee S. Cohen

[57] ABSTRACT

An electrosurgical hemostatic instrument is provided in which the coagulation status of tissue engaged by two elements delivering an electrosurgical energy to tissue may be observed, and in which damage from thermal spread may be minimized. A preferred embodiment of the invention provides a bipolar endoscopic clamping, coagulation and cutting device. The coagulation may be observed by exposed electrode tips at the distal end of the instrument, an open knife slot which permits the escape of vapor, plume, steam or smoke from the coagulation process, windows located in the first or second element through which coagulating tissue may be observed, indentation in one of the elements which exposes a tissue contacting surface of the other element; a temperature indication strip located on the distal end of the instrument, or a current indicator located on the instrument.

1 Claim, 7 Drawing Sheets

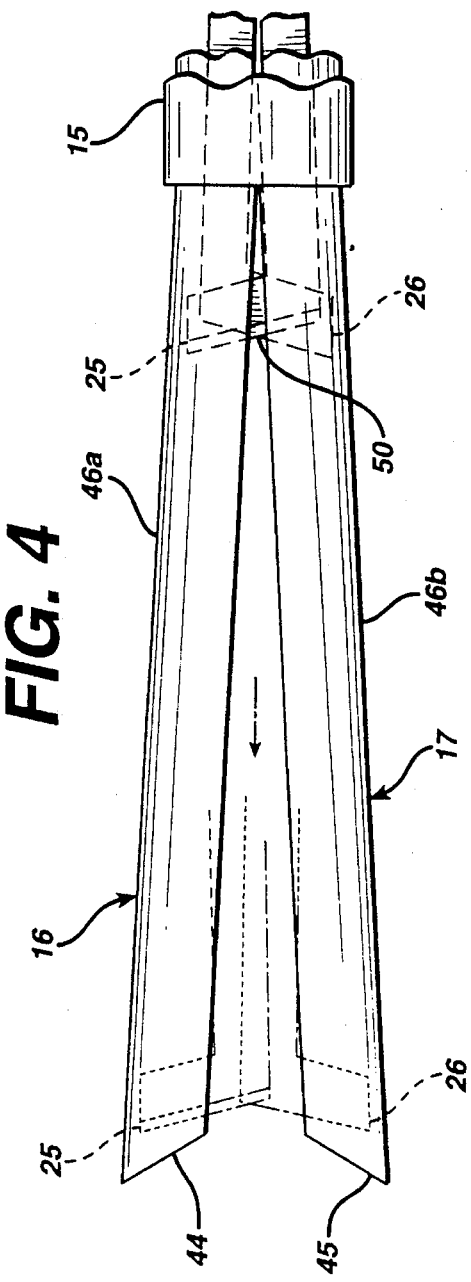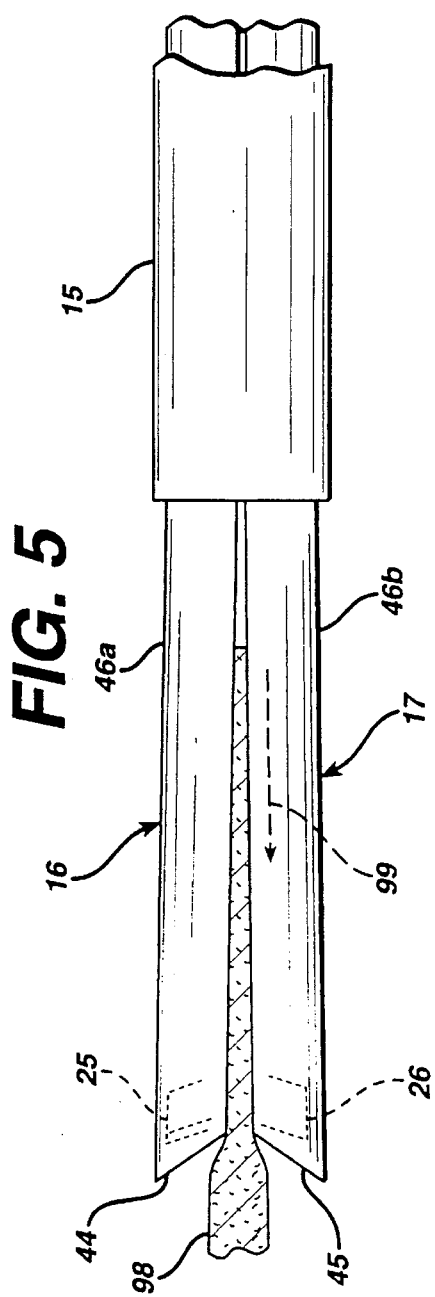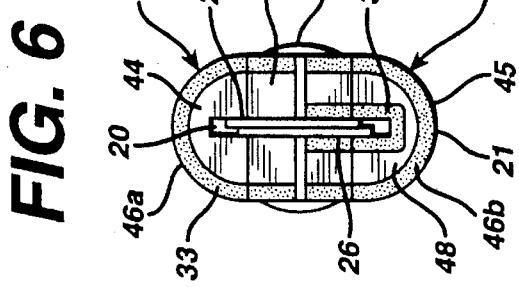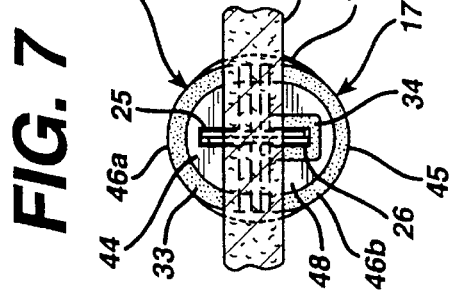

FIG. 8
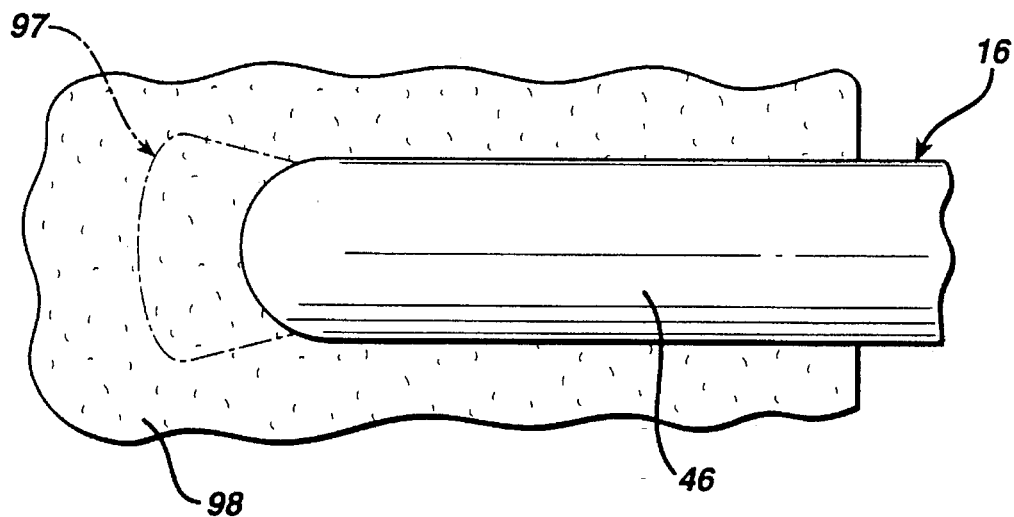
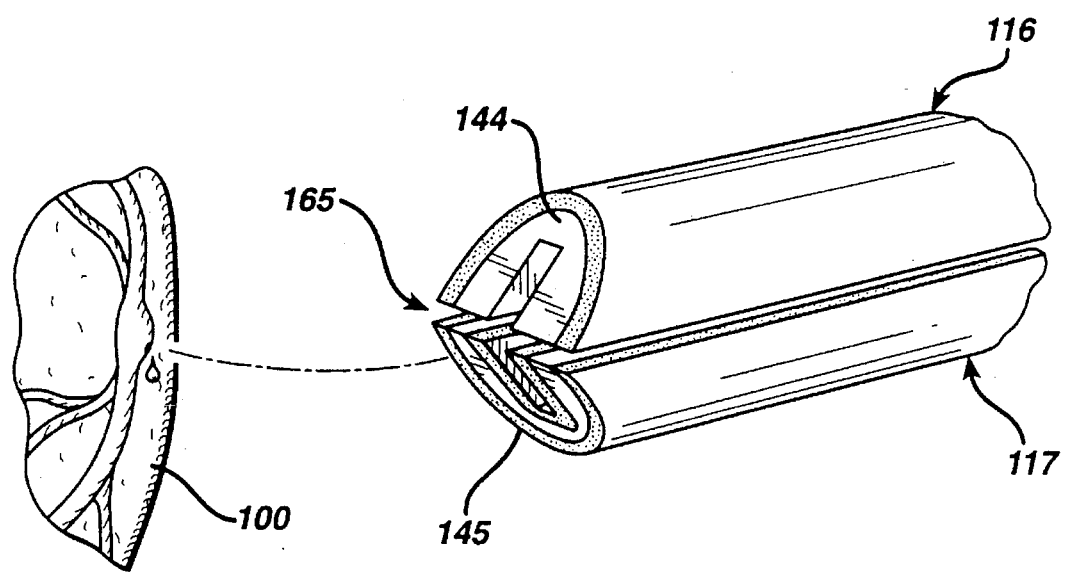
FIG. 9

5,599,350

ELECTROSURGICAL CLAMPING DEVICE WITH COAGULATION FEEDBACK

FIELD OF THE INVENTION

The present invention relates to an electrosurgical hemostatic grasping, clamping or forceps type device, and in particular the present invention relates to a clamping and cutting device with a feedback or monitoring feature for identifying the coagulation status of tissue being electrosurgically treated by the device.

BACKGROUND OF THE INVENTION

Electrosurgical hemostatic devices have been used for effecting improved hemostasis by heating tissue and blood vessels to cause coagulation or cauterization. Monopolar devices utilize one electrode associated with the cutting or cauterizing instruments and a remote return, usually adhered externally to the patient. More recently bipolar instruments have been used because the coagulating current is generally limited to the tissue between two poles or electrodes of the tissue treating portion of an instrument.

Bipolar forceps have also been used, particularly for coagulating tissue in various procedures. Generally bipolar forceps are comprised of two opposing jaws each of a different electrical potential. The jaws are used to grasp tissue between the two poles and apply electrical current through the grasped tissue. The forceps however tend to cause areas of thermal spread, i.e., dissipation of heat outside the area defined by the grasping or engaging surfaces of the forceps. Other drawbacks of known bipolar forceps include the tendency of current to arc between the electrodes or poles when tissue is too thin, or, the tendency of the forceps to short when the electrodes or poles of the forceps touch.

U.S. application Ser. No. 08/095,797 filed on Jun. 22, 1993, now U.S. Pat. No. 5,403,312, illustrates, in a preferred embodiment, a clamping and coagulating device in which most of the tissue being treated by the end effector of the device is not visible to the user. The electrodes in the preferred embodiment of this device are offset from each other with respect to the tissue grasping surfaces so that the likelihood of arcing or shorting is reduced. However, in this device it is difficult to visualize coagulation as it is occurring to the tissue unless thermal spread is occurring.

It is therefore an object of the present invention to provide an electrosurgical device in which the coagulation can be perceptibly monitored by a user of the device.

SUMMARY OF THE INVENTION

Accordingly, one embodiment of the present invention provides an electrosurgical hemostatic device which provides a visual indication of completed coagulation without requiring increased thermal spread or bilateral damage.

In one embodiment of a device the electrodes are configured so that the tissue tends to coagulate sequentially, proximal to distal. This progresses towards the tip of the jaws so that when discoloration of tissue at the tips is observed due to coagulation, the user can visually determine that tissue within the jaws has been coagulated. In one such embodiment visual feedback is provided at jaw tips or ends of a grasping or clamping device by exposing the ends of bipolar electrodes which otherwise form a current path which is substantially contained within the jaws or opposing elements of the device.

Another aspect of the invention provides an exposed knife slot or cutting element slot at the tip of the clamping and cutting device in which vapor, plume, steam or smoke produced during coagulation may escape. This aspect may also provide a source of feedback to a user who can visualize the amount of vapor or plume escaping from the knife slot.

Another aspect of the invention provides a bipolar cutting and coagulation device which may be used to grasp and treat tissue and then cut the tissue that has been treated. This device may also provide an electrode at the distal end or tip of the instrument so that when the jaws are closed the distal end or tip may be used to provide additional coagulation of tissue. This may be useful for "touch-up" work, or for stopping "slow bleeders", i.e., minor tissue bleeding.

Another embodiment of the invention provides a device in which windows are used on the device through which tissue in the zone of coagulation or an area through which current is passing, may be viewed.

In yet another embodiment of the present invention two opposing jaw members are provided in which the tissue contacting surface of one of the jaw members extends distally beyond the other jaw member to provide a stepped area or zone of enhanced visualization.

Yet another device provides a temperature strip or other temperature indicating device which is attached or adhered to an outer surface of the end effector. The temperature indicator changes color or hue as heat builds up in the end effector from the diversion heat energy from heated tissue to the metal components. Thus, the temperature indicates by heat when and where coagulation has been completed.

Alternatively, a liquid crystal thermometer may be used coupled with a low resistance heater or resistance wire connected in series with one of the electrodes to indicate that a level of current being delivered to the tissue. Using most conventional electrosurgical generators, the current will correlate to impedance, and impedance to coagulation status of the tissue. This LC thermometer may be located any where on the device where it is visible to a user.

These and other objects of the invention will be better understood from the following attached Detailed Description of the Drawings, when taken in conjunction with the Detailed Description of the Invention.

DETAILED DESCRIPTION OF THE DRAWINGS

FIG. 4 is illustrates a side view of the end effector illustrated in FIG. 1;

FIG. 5 illustrates a side view of the end effector illustrated in FIG. 1 as it is engaging and coagulating tissue;

FIG. 6 illustrates a front end view of FIG. 4;

FIG. 7 illustrates a front end view of FIG. 5;

FIG. 8 illustrates a top plan view of the end effector portion illustrated in FIGS. 4 and 5 as engaged tissue is being coagulated;

FIG. 9 illustrates a side perspective view of an alternative end effector of the device illustrated in FIG. 1 with the jaws closed, being used to spot treat tissue;

DETAILED DESCRIPTION OF THE INVENTION

Figure 1:
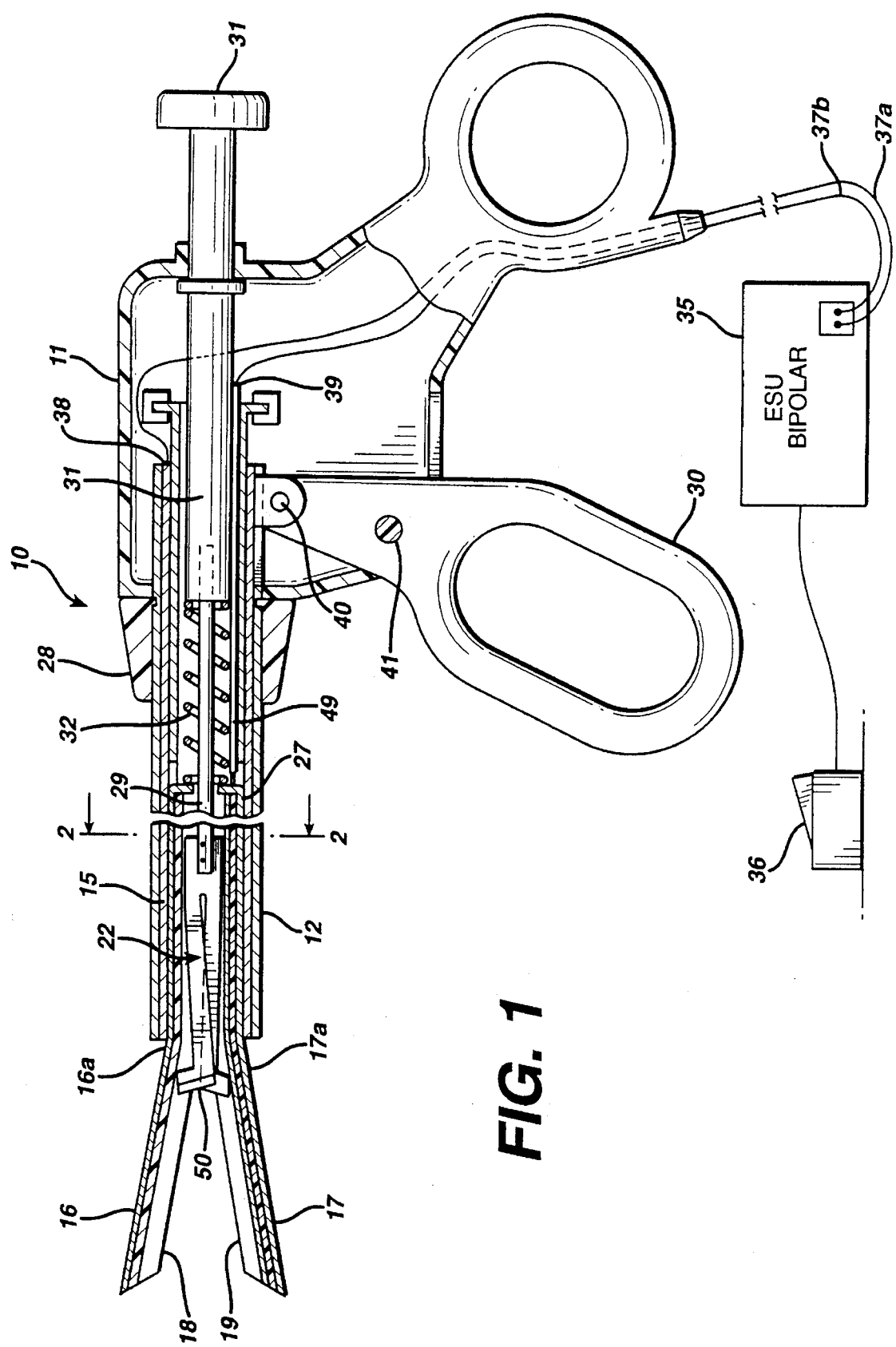
FIG. 1 is an elevated side cross-sectional view of a clamping, cutting and coagulating device of the present invention.
Figure 2:
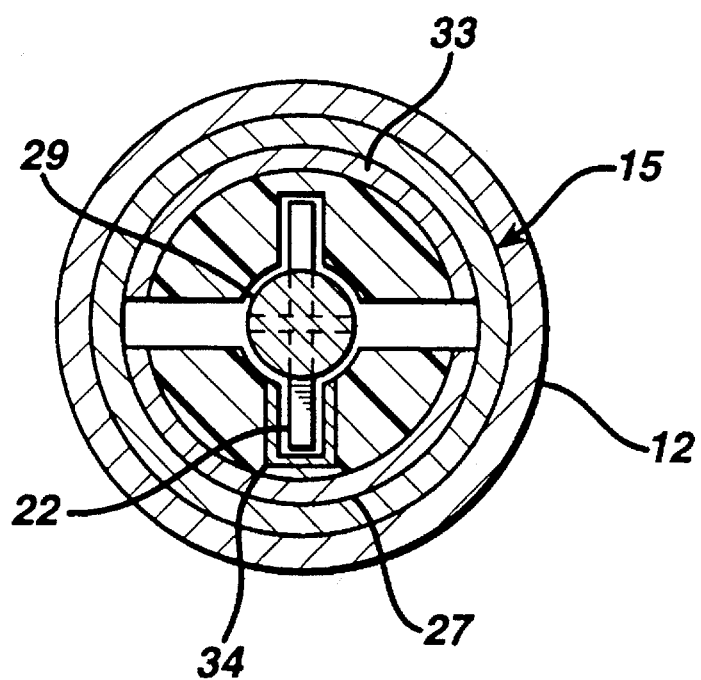
FIG. 2 is a cross-section of FIG. 1 along the lines 2—2.
Figure 3:
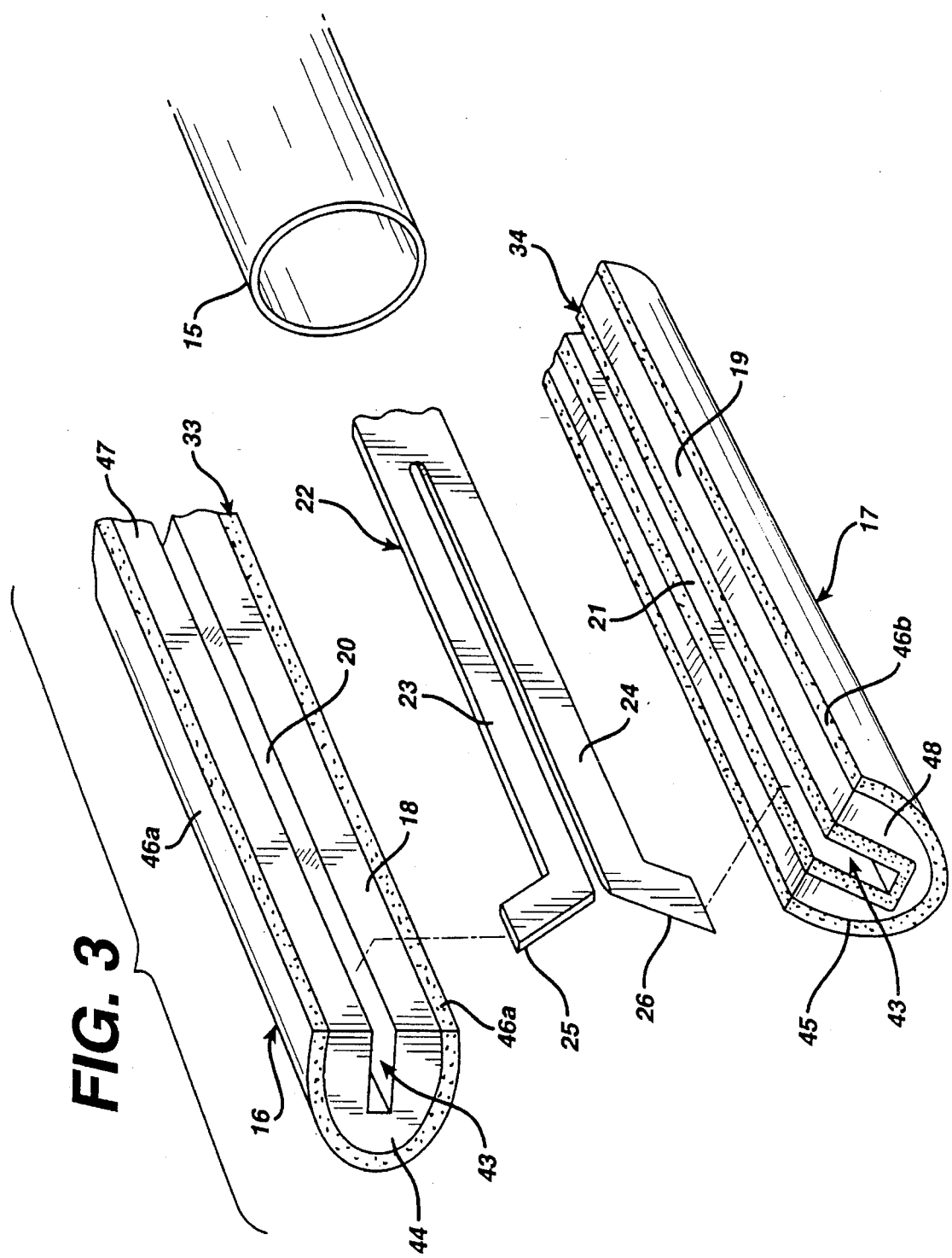
FIG. 3 is a perspective break away view of the distal portion of the device in FIG. 1.

Referring now to FIGS. 1–8 there is illustrated a clamping and cutting instrument 10 of the present invention. The instrument 10 comprises a housing 11, a hollow sheath 12 comprised of an electrically insulative material extending distally from the housing 11, a jaw closure tube 15 extending through the sheath 12, and clamping jaw members 16, 17 extending from the distal end of closure tube 15. Jaw members 16 and 17 include opposed surfaces 18, 19 which are arranged to close towards each other to approximate tissue therebetween, upon advancing the closure tube 15 over camming surfaces 16a, 17a of jaw member 16, 17 respectively. Jaw members 16, 17 include grooves 20, 21 formed therein respectively, for receiving cutting element 22 as it is advanced through jaw members 16, 17. Cutting element 22 includes prongs 23, 24 separated at the distal end of the cutting element 22. The distal end of each prong 23, 24 is formed into a cutting blade 25, 26, respectively.

Blades 25, 26 are arranged to ride within grooves 20, 21 respectively as the cutting element 22 is advanced through jaw members 16, 17. Prongs 23, 24 overlap each other so that together the blades 25, 26 form a shearing or cutting member 50 for shearing tissue. Blades 25, 26 are angled so that when the prongs 23, 24 overlap the blades 25, 26 form a V-shaped shearing member. The prongs 23, 24 comprise a spring in which one or both of the prongs 23, 24 are biased away from each so that the blades 25, 26 will tend to separate from each other as the gap between jaw members 16, 17 increases, i.e., with thicker tissues. As the gap increases, the area of overlap decreases and the cutting member 50 size expands or increase as illustrated in FIG. 4. As the gap decreases the area of overlap increases and the cutting member 50 size contracts or decreases as illustrated in FIG. 5.

Jaw members 16, 17 include electrodes 33, 34, respectively, forming a portion of surface 18, 19 respectively. In this preferred embodiment the electrodes are offset from each other so that they will not contact each other if tissue is thin and/or will prevent arcing between electrodes. Electrode 33 is of a different electrical potential than electrode 34. A generator 35 provides electrosurgical energy to the electrodes 33, 34 and is activated by a user controlled footswitch 36. The generator 35 is preferably an electrosurgical unit capable of providing bipolar energy. The energy is delivered through wires 37a, 37b which are coupled through housing 11, respectively, to contact 38 of the closure tube 15 and electrically insulated wire 39 extending through closure tube 15 to electrode 34.

A rotatable knob 28 extends from the housing 11. The knob engages sheath 12 and closure tube 15 which engages jaw members 16, 17. The knob 28 may be used to rotate the jaw members 16, 17 into position to grasp and clamp tissue.

After tissue is positioned between jaw members 16, 17 the jaw members 16, 17 are closed together to engage tissue between opposed surfaces of jaw members 16, 17. A pivoting handle member 30 is coupled to closure tube 15 and is arranged to rotate about pivot 41 to provide a translational longitudinal movement through linkage 40 to closure tube 15 over camming surface 16a, 17a, to close jaws together. Electrosurgical energy may then be supplied by activating footswitch 36.

After electrosurgical energy is applied and the tissue is electrosurgically treated to a desired degree, the cutting element 22 is advanced to cut the engaged tissue. The cutting element 22 is actuated by pusher knob 31 which extends from outside housing 11 into closure tube 15 in housing 11. Pusher knob 31 is then coupled to drive rod 29 which extends through closure tube 15 and couples on its distal end to the cutting element 22. A spring 32 located in closure tube 15 abuts against the distal end of the pusher knob 31 and against the proximal end 27 of jaw members 16, 17. Spring 32 provides for the automatic retraction of the cutting element 22 when the pusher knob 31 is released.

Referring now to FIGS. 4 and 6, top jaw 16 and bottom jaw 17 are in a spaced apart position arranged to grasp or position tissue therebetween. Jaw members 16, 17 are comprised of an outer metal casings 46a, 46b which act as first electrode 33 of a first electrical potential of a bipolar system. The closure tube 15 closes the jaws together as the tube 15 is advanced distally. The tube 15 is constructed of a conductive metal and contacts the outer casing 46a of jaw member 16 and outer casing 46b of jaw member 17. Jaw member 17 is further constructed of an insulative material 48 surrounded by outer casing 46b, and a U-shaped electrode 34 formed on the inside of the insulative material 48. The electrode 34 forms the lower half 21 or groove of a knife channel 43. The top jaw 16 also has an insulative material 47 formed on the inside of the metal casing 46. The insulative material 47 forms the top half 20 of knife channel 43. The electrodes 33, 34 are arranged so that when tissue is grasped and the jaws 16, 17 are closed together, electrodes 33, 34 are offset from each other with respect to interfacing surfaces 18, 19 of jaw members 16, 17 respectively. The distal end 44 of jaw member 16 has an inwardly angled shape and exposes electrode 33 as well top half 20 of knife channel 43. Similarly, the distal end 45 of jaw member 17 is angled inwardly and exposes electrodes 33, 34 and lower half 21 of knife channel 43. The inwardly angled distal ends 44, 45 form a V-shaped space at the distal ends 44, 45 of jaws 16, 17, which assists in channeling tissue in between jaws 16, 17.

FIG. 5 illustrates a side view of the end effector in FIG. 4 engaging tissue and applying electrosurgical energy. An arrow 99 indicates the proximal to distal direction of coagulation. It is believed that this directional coagulation progression results from the variation in compression and/or distance between electrodes due in part to the cantilevered arrangement of the jaw members from proximal to distal.

FIG. 8 illustrates the top view of the end effector grasping tissue 98 as it is being treated. An area of tissue 97 surrounding the distal end of the end effector is illustrated in which desiccation of and/or thermal effects on the tissue may be visualized. Alternatively, or in addition, vapor or plume may be visualized escaping through grooves 20, 21 of knife channel or slot 43 as tissue is coagulated.

FIG. 9 illustrates an alternative embodiment of the present invention. An end effector is shown with jaw members 116, 117 in a closed position. The distal ends 144, 145 of jaw members 116, 117 respectively are angled to form a V-shaped tip 165 at the distal end of the end effector. This tip 165 may be used to coagulate sites where bleeding is occurring in tissue 100. The end effector of FIG. 9 is oriented in an opposite manner as the end effector in FIG. 4. The end effector of FIG. 9 is arranged so that the distal ends 144 and 145 are angled outward i.e., so that they form a single tip 165 for controlled manipulation and use of the distal end of the end effector as a coagulator.

Figure 10:
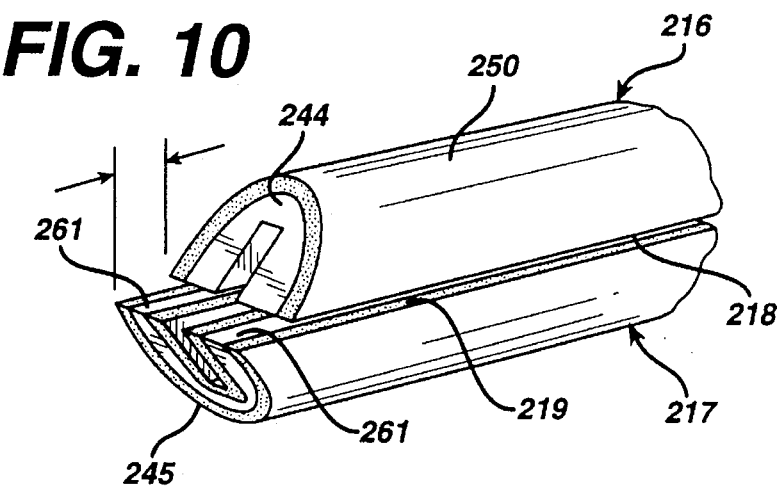
FIG. 10 illustrates an alternative embodiment of the end effector of the device illustrated in FIG. 1.

FIG. 10 illustrates yet another embodiment of the end effector of the device illustrated in FIG. 1. The end effector in FIG. 10 is arranged as the end effector in FIG. 9 except that the distal ends 244, 245 of jaw members 216, 217 respectively are offset from each other proximal to distal so that jaw member 217 extends distally beyond the end 244 of jaw member 216. Thus, the outer surface 250 of jaw 216 is recessed at a plane of the tissue contacting surface 218 of jaw 216, or, a portion of the surface 218 is recessed with respect to a plane of said surface, to expose a portion of tissue contacting surface 219 of opposing jaw member 217. This forms a step zone 261 on inner surface 219 of end effector 217. Thus, the step zone 261 provides an enhanced visualization of coagulation as the tissue contacting surface 219 through which current is delivered is in contact with tissue that may be seen by the user.

Figure 11:
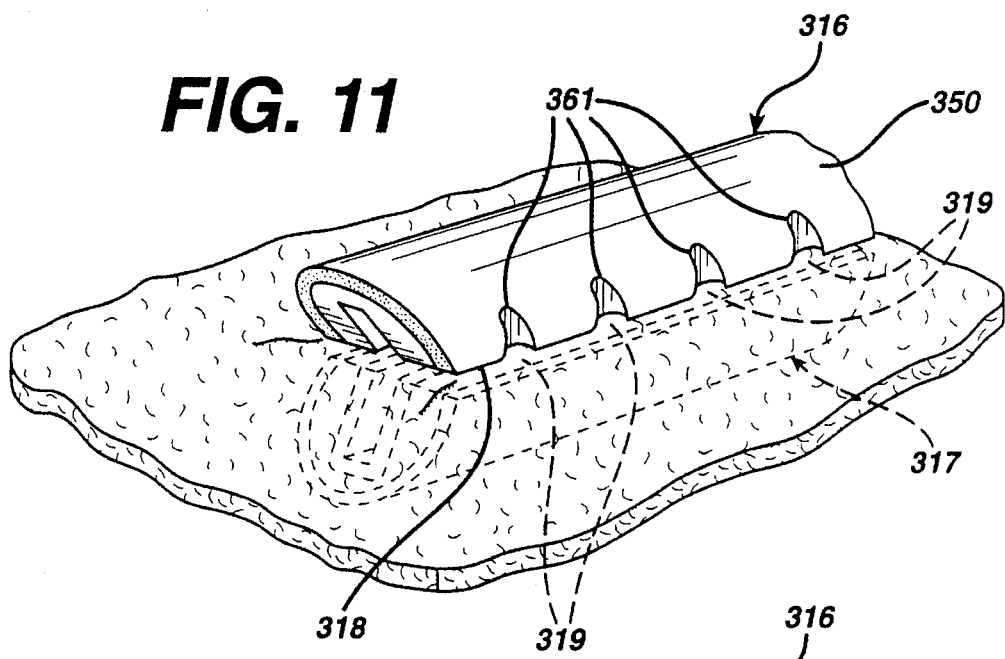
FIG. 11 illustrates an alternative embodiment of the end effector of the device illustrated in FIG. 1.

FIG. 11 illustrates another embodiment of the end effector of the present invention. The side of the jaw 316 includes notches 361 which expose portions of the tissue contacting surface 319 of the opposing jaw 317. Thus, the outer surface 350 of jaw 316 is recessed at a plane of the tissue contacting surface 318 of jaw 316, or, a portion of the surface 318 is recessed with respect to a plane of said surface, to expose a portion of tissue contacting surface 319 of opposing jaw member 317.

Figure 12:
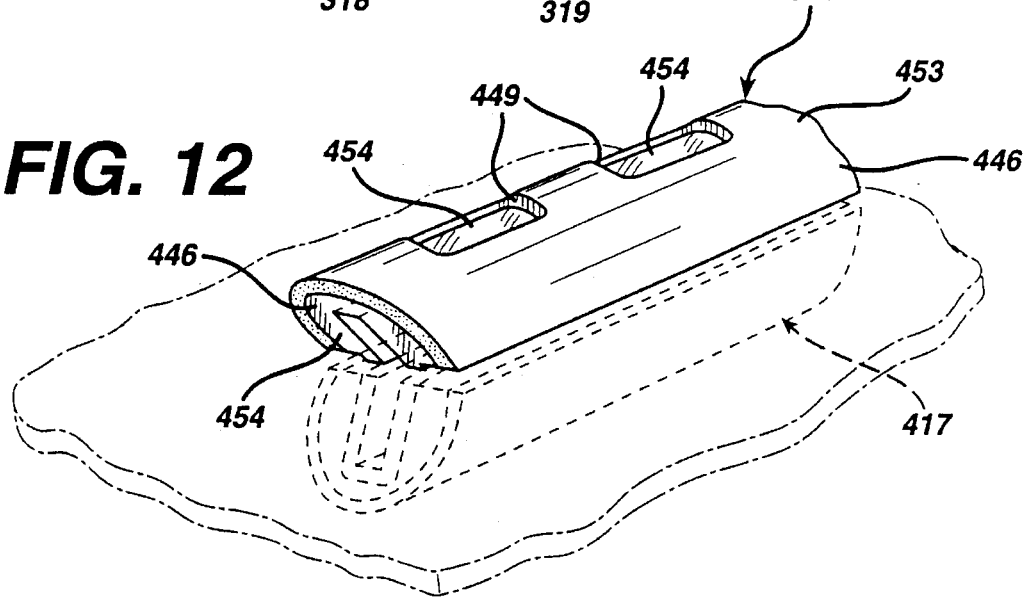
FIG. 12 illustrates an alternative embodiment of the end effector of the device illustrated in FIG. 1.

FIG. 12 illustrates an alternative embodiment of end effector of the device in FIG. 1. The upper jaw 416 includes windows 449 formed in the top or outer surface 453 of the metal casing 446 that forms the top jaw 416. The insulation 454 is formed of a transparent or translucent material such as transparent ceramic (e.g. a glass), or plastic (e.g. a clear polycarbonate), which permits the user to see the tissue engaged between the jaws 416, 417, through windows 449.

Figure 13:
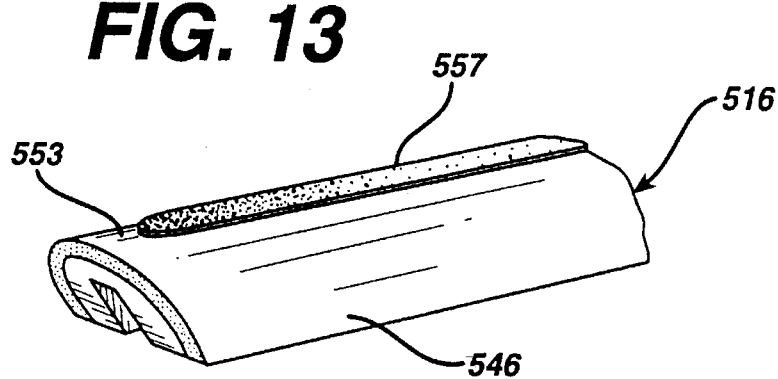
FIG. 13 illustrates an alternative embodiment of the end effector of the device illustrated in FIG. 1.

FIG. 13 illustrates the top jaw 516 of yet another alternative embodiment of an end effector of the present invention. Jaw member 516 includes a temperature indicator 557 adhered to the top or outer surface 553 of the metal casing 546 which forms jaw member 516. The temperature indicator 557 may be formed of indicators which are known in the art such as Omegalabel® Temperature Monitors or liquid crystal temperature monitors. The temperature indicator 557 changes color as heat builds up in the jaw, from the heated, coagulated tissue diverting energy into the metal components. The user then may see where and when the jaw member 516 is heating up.

Figure 14:
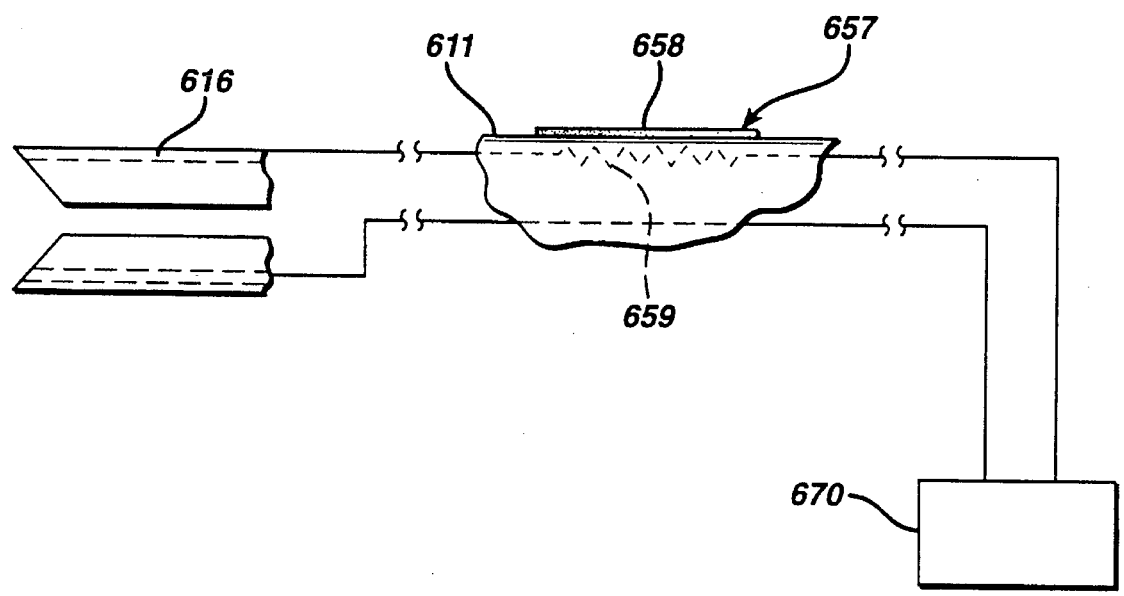
FIG. 14 illustrates an alternative embodiment of the present invention.

FIG. 14 illustrates another embodiment. A current indicator 657 is shown located on the instrument handle or housing 611 (although, the indicator may be located elsewhere on the device including the generator or connections between generator and instrument housing). The indicator 657 includes a liquid crystal thermometer 658 adjacent a low resistance heater wire 659 through which current flows as it is returned from or delivered to end effector electrode 616 from generator 670. The liquid crystal 658 thus would indicate a higher temperature for a higher current flow and a lower temperature for a lower current flow. Using a conventional electrosurgical generator, the indicator 657 would indicate tissue impedance level which indicates tissue coagulation status.

Several variations of this invention have been described in connection with specific embodiments involving a bipolar endoscopic clamping and cutting device. Naturally, the invention may be used in numerous applications where hemostasis is desired and in which indication of tissue coagulation may be perceived by a user. Accordingly, it will be understood by those skilled in the art that various changes in modifications may be made in the invention without departing from its scope, which is defined by the following claims and their equivalents.

We claim:

1. An electrosurgical instrument comprising:

a shaft having a distal end and a longitudinal axis;

an end effector located at the distal end of the shaft, adapted to receive bipolar energy therein, said end effector comprising:

a distal end; and first and second elements comprising first and second opposed tissue contacting surfaces respectively and first and second outer surfaces respectively, said tissue contacting surfaces moveable relative to each other from an open, spaced-apart position for positioning tissue therebetween, to a closed position for approximating the tissue, at least a portion of one of said tissue contacting surfaces comprising a first electrode, and at least a portion of one of said tissue contacting surfaces comprising an electrically isolated second electrode; and a temperature sensor coupled to at least one outer surface of said elements, said temperature sensor arranged to provide visual indication of the temperature of said end effector.

* * * * *